US00PP23961P2

(12) United States Plant Patent
Wood

(10) Patent No.: US PP23,961 P2
(45) Date of Patent: Oct. 8, 2013

(54) ***EUONYMUS* PLANT NAMED 'ALBAN'**

(50) Latin Name: *Euonymus fortunei*
Varietal Denomination: Alban

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 44 days.

(21) Appl. No.: 13/385,294

(22) Filed: Feb. 10, 2012

(51) Int. Cl.
*A01H 5/00* (2006.01)

(52) U.S. Cl.
USPC ..... Plt./246

(58) Field of Classification Search
USPC ..... Plt./246
See application file for complete search history.

(56) References Cited

U.S. PATENT DOCUMENTS

PP4,766 P * 9/1981 Corliss ..... Plt./246
PP13,852 P3 * 5/2003 van Heesbeen ..... Plt./246

OTHER PUBLICATIONS

Anonymous. "White Album *Euonymus fortunei*" available at http://provenwinners.com/plants/euonymus/white-album-euonymus-fortunei accessed May 20, 2013.*
UPOV PLUTO citation for 'Alban'.*

* cited by examiner

*Primary Examiner* — Wendy C Haas
(74) *Attorney, Agent, or Firm* — C. A. Whealy

(57) ABSTRACT

A new and distinct cultivar of *Euonymus* plant named 'Alban', characterized by its upright, outwardly spreading and mounding plant habit; freely branching habit; dense and bushy plant form; and relatively large variegated leaves.

1 Drawing Sheet

Botanical designation: *Euonymus fortunei.*
Cultivar denomination: 'ALBAN'.

BACKGROUND OF THE INVENTION

The present invention relates to a new and distinct cultivar of *Euonymus* plant, grown as an ornamental shrub, botanically known as *Euonymus fortunei* and hereinafter referred to by the name 'Alban'.

The new *Euonymus* plant is a naturally-occurring branch mutation of *Euonymus fortunei* 'Emerald Gaiety', not patented. The new *Euonymus* plant was discovered and selected by the Inventor in 2001 as a single plant from within a population of plants of 'Emerald Gaiety' in an outdoor nursery in Grand Haven, Mich.

Asexual reproduction of the new *Euonymus* plant by softwood cuttings in a controlled environment in Grand Haven, Mich. since September, 2001 has shown that the unique features of this new *Euonymus* plant are stable and reproduced true to type in successive generations.

SUMMARY OF THE INVENTION

Plants of the new *Euonymus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Alban'. These characteristics in combination distinguish 'Alban' as a new and distinct *Euonymus* plant:

1. Upright, outwardly spreading and mounding plant habit.
2. Freely branching habit; dense and bushy plant form.
3. Relatively large variegated leaves.

Plants of the new *Euonymus* differ primarily from plants of the mutation, 'Emerald Gaiety', in the following characteristics:

1. Plants of the new *Euonymus* are more uniform than and not as sprawling as plants of 'Emerald Gaiety'.
2. Plants of the new *Euonymus* have larger leaves than plants of 'Emerald Gaiety'.
3. Leaves of plants of the new *Euonymus* and 'Emerald Gaiety' differ in variegation pattern.

Plants of the new *Euonymus* can be compared to plants of *Euonymus* 'Emerald n' Gold', not patented. Plants of the new *Euonymus* differ from plants of 'Emerald n' Gold' in the following characteristics:

1. Plants of the new *Euonymus* have larger leaves than plants of 'Emerald n' Gold'.
2. Plants of the new *Euonymus* and 'Emerald n' Gold' differ in variegation pattern and leaf color.

BRIEF DESCRIPTION OF THE PHOTOGRAPH

The accompanying colored photograph illustrates the overall appearance of the new *Euonymus* plant showing the colors as true as it is reasonably possible to obtain in colored reproductions of this type. Colors in the photograph may differ slightly from the color values cited in the detailed botanical description which accurately describe the colors of the new *Euonymus* plant.

The photograph comprises a side perspective view of a typical plant of 'Alban' grown in a container.

DETAILED BOTANICAL DESCRIPTION

The aforementioned photograph and following observations, measurements and values describe plants grown during the spring and summer in 20-cm containers in an outdoor nursery in Grand Haven, Mich. and under cultural practices typical of commercial *Euonymus* production. Plants were two years old when the photograph and description were taken. In the following description, color references are made to The Royal Horticultural Society Colour Chart, 2001 Edition, except where general terms of ordinary dictionary significance are used.

Botanical classification: *Euonymus fortunei* 'Alban'.

Parentage: Naturally-occurring branch mutation of *Euonymus fortunei* 'Emerald Gaiety', not patented.

Propagation:

*Type.*—By softwood cuttings.

*Time to initiate roots, summer.*—About one month at temperatures of 20° C.

*Time to initiate roots, winter.*—About two months at temperatures of 18° C.

*Time to produce a rooted young plant, summer.*—About four months at temperatures of 20° C.

*Time to produce a rooted young plant, winter.*—About six months at temperatures of 18° C.

*Root description.*—Medium in thickness, fibrous.

*Rooting habit.*—Freely branching; dense.

Plant description:

*Plant and growth habit.*—Upright, outwardly spreading and mounding plant habit; freely branching habit, about 87 lateral branches per plant; pinching enhances lateral branch development; dense and bushy appearance; moderately vigorous growth habit.

*Plant height.*—About 20 cm.

*Plant width* (*spread*).—About 40 cm.

*Lateral branches.*—Length: About 13 cm. Diameter: About 2 mm. Internode length: About 2 cm. Strength: Strong, flexible. Aspect: Erect to about 45° from vertical. Texture: Smooth, glabrous. Color, developing: Close to 138C. Color, developed: Close to 177A.

Foliage description:

*Arrangement.*—Opposite, simple.

*Length.*—About 4 cm.

*Width.*—About 2 cm.

*Shape.*—Elliptical to slightly ovate.

*Apex.*—Acute.

*Base.*—Obtuse.

*Margin.*—Serrulate.

*Texture, upper and lower surfaces.*—Smooth, glabrous; waxy.

*Venation pattern.*—Pinnate.

*Color.*—Developing leaves, upper surface: Center, close to 146A; towards the margins, close to 160B. Developing leaves, lower surface: Center, close to 147C; towards the margins, close to 160B. Fully developed leaves, upper surface: Center, close to 146A; towards the margins, close to 160B and 155A; midvein, close to 141B; lateral venation, similar to lamina colors. Fully developed leaves, lower surface: Center, close to 147C; towards the margins, close to 160B and 155A; midvein, close to 141B; lateral venation, similar to lamina colors.

*Petiole.*—Length: About 5 mm. Diameter: About 1 mm. Texture, upper and lower surfaces: Smooth, glabrous. Color, upper and lower surfaces: Close to 141B.

Flower description: Flower initiation and development has not been observed on plants of the new *Euonymus.*

Disease & pest resistance: Plants of the new *Euonymus* have not been noted to be resistant to pathogens and pests common to *Euonymus.*

Temperature tolerance: Plants of the new *Euonymus* have been observed to tolerate temperatures from about −10° C. to about 35° C.

It is claimed:

1. A new and distinct *Euonymus* plant named 'Alban' as illustrated and described.

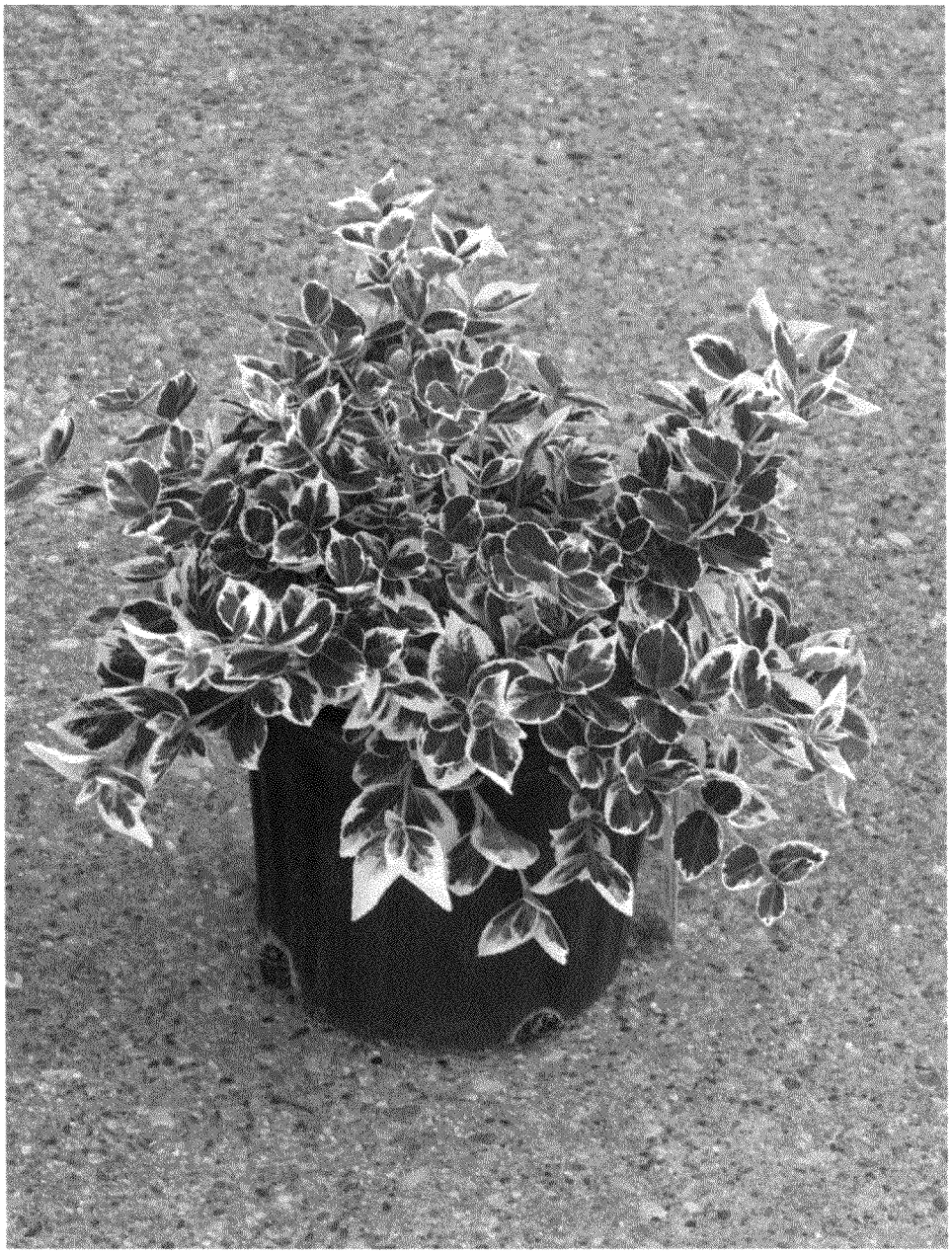

* * * * *